(12) United States Patent
Abe et al.

(10) Patent No.: US 12,661,061 B2
(45) Date of Patent: Jun. 23, 2026

(54) SLEEP ESTIMATION DEVICE, SLEEP ESTIMATION SYSTEM, WEARABLE INSTRUMENT, AND SLEEP ESTIMATION METHOD

(71) Applicants: KYOCERA Corporation, Kyoto (JP); University of Tsukuba, Tsukuba (JP)

(72) Inventors: Takashi Abe, Tsukuba (JP); Zhiwei Fan, Tsukuba (JP); Takahiro Watanabe, Kyoto (JP)

(73) Assignees: KYOCERA Corporation, Kyoto (JP); University of Tsukuba, Tsukuba (JP)

( * ) Notice: Subject to any disclaimer, the term of this patent is extended or adjusted under 35 U.S.C. 154(b) by 576 days.

(21) Appl. No.: 18/019,659

(22) PCT Filed: Aug. 6, 2021

(86) PCT No.: PCT/JP2021/029351
§ 371 (c)(1),
(2) Date: Feb. 3, 2023

(87) PCT Pub. No.: WO2022/030623
PCT Pub. Date: Feb. 10, 2022

(65) Prior Publication Data
US 2023/0284969 A1 Sep. 14, 2023

(30) Foreign Application Priority Data
Aug. 6, 2020 (JP) .................................. 2020-133828

(51) Int. Cl.
*A61B 5/00* (2006.01)
*A61B 5/0205* (2006.01)
(Continued)

(52) U.S. Cl.
CPC .......... *A61B 5/4812* (2013.01); *A61B 5/0205* (2013.01); *A61B 5/7257* (2013.01);
(Continued)

(58) Field of Classification Search
CPC ... A61B 5/4812; A61B 5/0205; A61B 5/7257; A61B 5/7267; A61B 5/7278; A61B 5/0261; A61B 5/11; A61B 2562/0219
See application file for complete search history.

(56) References Cited

U.S. PATENT DOCUMENTS 10,827,972 B1 * 11/2020 Ayers ................... A61B 5/0059
2014/0180114 A1 6/2014 Chen et al.
(Continued)

FOREIGN PATENT DOCUMENTS

JP 2013-165828 A 8/2013
JP 2014-530642 A 11/2014
(Continued)

OTHER PUBLICATIONS

Xiao, M., et al., Sleep stages classification based on heart rate variability and random forest, Biomedical Signal Processing and Control, 8(5), Nov. 1, 2013, pp. 624-633, XP093132350, NL, ISSN: 1746-8094, DOI: 10.1016/j.bspc.2013.06.001, [online] URL:https://www.sciencedirect.com/science/article/pii/S1746809413000864/pdfft?md5=a490ac1cc0e9df3f3fa3daccf4c13d0b&pid=1-s2.0-S1746809413000864-main.pdf>.

*Primary Examiner* — Amanda L Steinberg
(74) *Attorney, Agent, or Firm* — Procopio, Cory, Hargreaves & Savitch LLP

(57) ABSTRACT

A stage of sleep is easily estimated. A sleep estimation device includes a first acquisition unit configured to acquire blood flow data, a generation unit configured to generate a frequency spectrum of the blood flow data by performing frequency analysis processing on the blood flow data, and a first determination unit configured to determine a stage of sleep of a subject based on the frequency spectrum.

10 Claims, 8 Drawing Sheets

(51) Int. Cl.
    *A61B 5/026*         (2006.01)
    *A61B 5/11*          (2006.01)

(52) U.S. Cl.
    CPC .......... *A61B 5/7267* (2013.01); *A61B 5/7278*
        (2013.01); *A61B 5/0261* (2013.01); *A61B 5/11*
           (2013.01); *A61B 2562/0219* (2013.01)

(56)             References Cited

U.S. PATENT DOCUMENTS

| 2016/0007916 A1 | 1/2016 | Twawaki | |
| 2016/0100792 A1 | 4/2016 | Ding | |
| 2016/0302737 A1 | 10/2016 | Watson et al. | |
| 2017/0215808 A1* | 8/2017 | Shimol | A61B 5/0205 |
| 2018/0064388 A1* | 3/2018 | Heneghan | A61B 5/743 |
| 2019/0336068 A1 | 11/2019 | Bozkurt et al. | |
| 2020/0397365 A1* | 12/2020 | Zhang | G16H 50/20 |

FOREIGN PATENT DOCUMENTS

| JP | 2018-161432 A | 10/2018 |
| JP | 2019-118524 A | 7/2019 |

* cited by examiner

SLEEP ESTIMATION DEVICE, SLEEP ESTIMATION SYSTEM, WEARABLE INSTRUMENT, AND SLEEP ESTIMATION METHOD

TECHNICAL FIELD

The present disclosure relates to estimation of a stage of sleep of a subject.

BACKGROUND OF INVENTION

Patent Document 1 discloses a technology for detecting a stage of sleep.

CITATION LIST

Patent Literature

Patent Document 1: JP 2018-161432 A

SUMMARY

A sleep estimation device according to an aspect of the present disclosure includes a first acquisition unit configured to acquire blood flow data indicating a blood flow of a subject, a generation unit configured to generate a frequency spectrum of the blood flow data by performing frequency analysis processing on the blood flow data, and a first determination unit configured to determine a stage of sleep of the subject based on the frequency spectrum.

A sleep estimation device according to an aspect of the present disclosure includes an acquisition unit configured to acquire blood flow data indicating a blood flow of a subject, a generation unit configured to generate processed data indicating a result of time-frequency analysis processing on the blood flow data by performing wavelet transform processing or short-time Fourier transform processing, in which an intensity in a predetermined frequency band is relatively emphasized compared with other frequency bands, on the blood flow data, and a determination unit configured to determine a stage of sleep of the subject based on the processed data.

A sleep estimation method according to an aspect of the present disclosure includes acquiring blood flow data indicating a blood flow of a subject, generating a frequency spectrum of the blood flow data by performing frequency analysis processing on the blood flow data, and determining a stage of sleep of the subject based on the frequency spectrum.

A sleep estimation method according to an aspect of the present disclosure includes acquiring blood flow data indicating a blood flow of a subject, generating processed data indicating a result of time-frequency analysis processing on the blood flow data by performing wavelet transform processing or short-time Fourier transform processing, in which an intensity in a predetermined frequency band is relatively emphasized compared with other frequency bands, on the blood flow data, and determining a stage of sleep of the subject based on the processed data.

DESCRIPTION OF EMBODIMENTS

Determination (estimation) of a stage of sleep of a subject according to the present disclosure is described below. First, the principle of determining the stage of sleep of the subject according to the present disclosure is described. Noted that when "A to B" is described in this specification, it indicates "from A to B". In this specification, blood flow waveform data is described as an example of blood flow data used for determining the stage of sleep.

Principle

Figure 2:
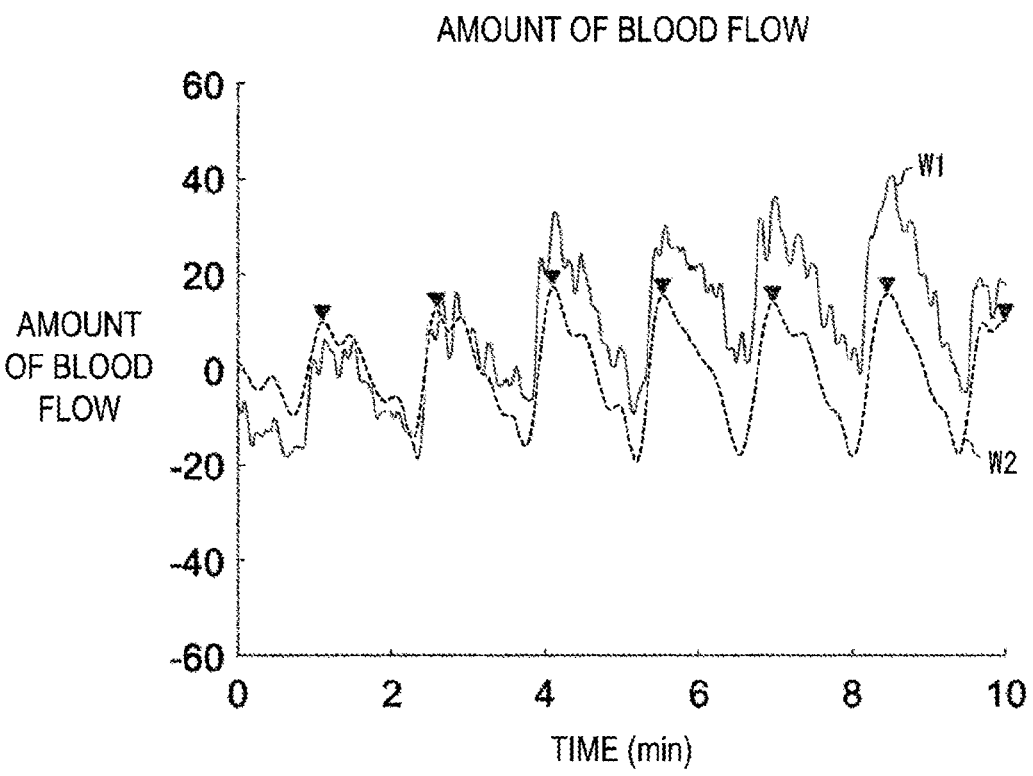
FIG. 2 is a graph showing an example of blood flow waveform data detected by a blood flow meter.

FIG. 2 is a graph showing an example of blood flow waveform data detected by a blood flow meter. In FIG. 2, the vertical axis indicates a value proportional to the amount of blood flow per hour [units: dimensionless], and the horizontal axis indicates measurement time [units: min]. The blood flow meter can acquire raw waveform data W1 and processed waveform data W2 as shown in FIG. 2 as the blood flow waveform data. The processed waveform data W2 is waveform data obtained by processing the raw waveform data W1 so that a peak of an R wave is easily acquired. The processed waveform data W2 is generated by, for example, smoothing the raw waveform data W1. In the processed waveform data W2, the time interval between adjacent peaks (amounts of blood flow at positions indicated by inverted triangles in the drawing) indicates a heartbeat interval (RRI: R-R Interval). Also in the raw waveform data W12 for a heartbeat shown in FIG. 4, the time interval between adjacent peaks (amounts of blood flow at positions indicated by the inverted triangles in the drawing) indicates a heartbeat interval (RRI).

The blood flow meter for detecting blood flow waveform data is a sensor that can detect blood flow waveform data indicating the blood flow of a subject by receiving scattered light generated by irradiating blood vessels of the subject with light. The blood flow meter may include a light emitting unit for irradiating the blood vessels of the subject with light, and a light receiving unit for receiving the scattered light.

Generally, when a fluid is irradiated with a laser beam, the irradiated laser beam is scattered by (i) a scatterer included in the fluid and moving with the fluid and (ii) a stationary object, such as a tube, through which the fluid flows, and scattered light is generated. Generally, the scatterer causes non-uniformity of the complex index of refraction in the fluid.

Due to the Doppler effect corresponding to the flow speed of the scatterer, the scattered light generated by the scatterer moving with the fluid is subject to a wavelength shift. On the other hand, the scattered light generated by the stationary object undergoes no wavelength shift. Since scattered light generated by the scatterer and scattered light generated by the stationary object cause optical interference, an optical beat is observed.

The blood flow meter may be a sensor using this phenomenon. That is, the blood flow meter may be a laser Doppler blood flow meter that detects, as blood flow waveform data, an optical beat caused by scattered light generated in the blood as a fluid by irradiating the blood vessels of the subject with a laser beam.

More specifically, a processor included in the blood flow meter may analyze an acquired light reception signal and calculate frequency analysis data indicating a signal intensity for each frequency of the light reception signal. As an example, the processor may analyze the acquired light reception signal by using a method such as fast Fourier transformation (FFT).

The processor may further generate blood flow waveform data indicating a variation pattern of the amount of blood flow of the subject on the basis of the frequency analysis data. As an example, the processor may calculate a primary moment sum X of the acquired frequency analysis data as blood flow waveform data. More specifically, the processor may calculate the primary moment sum X of the acquired frequency analysis data by using the following formula. The processor may calculate the primary moment sum X in a partial frequency band (for example, 1 to 20 kHz) by using the following formula: $X=\Sigma fx \times P(fx)$. Where, "fx" denotes a frequency and "P(fx)" denotes a value of a signal intensity at the frequency fx.

The primary moment sum X calculated by the processor on the basis of the frequency analysis data may be a value proportional to the amount of blood flow of the subject. The processor may generate pattern data indicating a variation pattern of the amount of blood flow of the subject over time by calculating the primary moment sum X for each of a plurality of the frequency analysis data. The processor may also generate blood flow waveform data by using data included in a partial frequency band among data included in the frequency analysis data. The processor can output the generated blood flow waveform data.

The blood flow waveform data may include data on at least one of cardiac output and the coefficient of variation of vasomotion, in addition to the amount of blood flow. Cardiac output represents the amount of blood delivered in one beat of the heart. Vasomotion represents a contraction-expansion movement of the blood vessel that occurs spontaneously and rhythmically. The coefficient of variation of vasomotion represents a value indicating, as a variation, the change in the amount of blood flow occurring on the basis of the vasomotion.

The blood flow waveform data may include a pulse wave.

Figure 3:
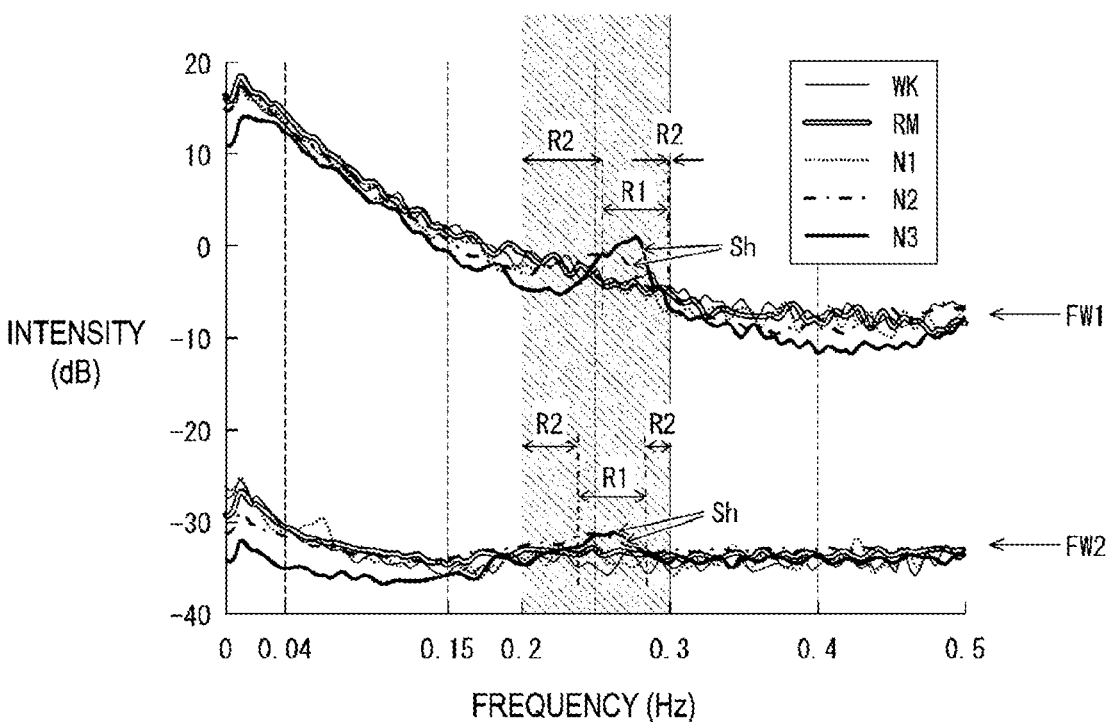
FIG. 3 is a graph showing an example of a frequency spectrum generated by performing Fourier transform processing on the blood flow waveform data.

FIG. 3 is a graph showing an example of a frequency spectrum generated by performing Fourier transform processing on the blood flow waveform data as shown in FIG. 2. The vertical axis indicates the intensity of a frequency spectrum [units: dB], and the horizontal axis indicates frequency [units: Hz]. Fourier transform processing is an example of frequency analysis processing, and is a process for generating a frequency spectrum of waveform data including no temporal changes.

FIG. 3 illustrates frequency spectra FW1 and FW2 corresponding to each stage of sleep. The frequency spectrum FW1 is a frequency spectrum generated as a result of performing Fourier transform processing on the raw waveform data W1. The frequency spectrum FW2 is a frequency spectrum generated as a result of performing Fourier transform processing on the heartbeat interval (RRI) of the processed waveform data W2.

The stages of sleep can be classified into three stages, namely, wakefulness, REM sleep, and non-REM sleep. Non-REM sleep can be further classified into stage 1 (N1), stage 2 (N2), and stage 3 (N3) from the lightest stage of sleep. REM sleep is sleep involving rapid eye movement (REM). Non-REM sleep is sleep involving no rapid eye movement.

This classification is performed on the basis of brain wave data detected by an electroencephalograph attached to the subject. Brain waves are classified into $\beta$ waves, $\alpha$ waves, $\theta$ waves, and $\delta$ waves in ascending order of wavelength. The $\beta$ wave is a brain wave with a frequency of about 38 to 14 Hz, for example. The a wave is a brain wave with a frequency of about 14 to 8 Hz, for example. The $\theta$ wave is a brain wave with a frequency of about 8 to 4 Hz, for example. The $\delta$ wave is a brain wave with a frequency of about 4 to 0.5 Hz, for example.

A person is asleep when the $\theta$ wave and the $\delta$ wave are dominant relative to the $\beta$ wave and the a wave. Here, the expression "are dominant" means that the percentage of a certain wave is large in the measured brain waves. The dominant brain wave is known to periodically change in the range of the $\theta$ wave and the $\delta$ wave during sleep. When the percentage of the $\theta$ wave included in the brain waves is less than a predetermined value, a person is in the state of REM sleep, and when the percentage of the $\theta$ wave is equal to or greater than a predetermined value and when the $\delta$ wave is dominant, a person is in the state of non-REM sleep. Stage 1 represents, for example, a state in which the $\alpha$ wave is equal to or less than 50%, and various low-amplitude frequencies are mixed. Stage 2 represents, for example, a state in which an irregular low-amplitude $\theta$ wave and $\delta$ wave appear, but no high-amplitude slow wave exists. Stage 3 represents, for example, a state in which a slow wave of equal to or less than 2 Hz and 75 $\mu$V is 20% or more. A state in which a slow wave of equal to or less than 2 Hz and 75 $\mu$V is 50% or more may be referred to as stage 4.

In FIG. 3, as the stages of sleep, wakefulness is indicated by "WK", REM sleep is indicated by "RM", stage 1 of non-REM sleep is indicated by "N1", stage 2 of non-REM sleep is indicated by "N2", and stage 3 of non-REM sleep is indicated by "N3".

As shown in the frequency spectra FW1 and FW2 in FIG. 3, a significant intensity change is recognized in a frequency band (predetermined frequency band) of 0.2 to 0.3 Hz in the frequency spectrum obtained from the subject who is in stages 2 and 3 of sleep. In other words, in the frequency spectrum, an intensity in a first range R1, which is a part of the frequency band of 0.2 to 0.3 Hz, is equal to or greater than an intensity in a second range R2, other than the first range R1, by a predetermined value. Hereinafter, the intensity in the first range R1 is referred to as a first intensity and the intensity in the second range R2 is referred to as a second intensity.

The first intensity may be, for example, a maximum intensity in the frequency band of 0.2 to 0.3 Hz. The second intensity may be, for example, a maximum intensity in the second range R2 other than the first range R1 (for example, about ±0.02 Hz centered on the maximum intensity, but within the frequency band of 0.2 to 0.3 Hz) including the maximum intensity. When a characteristic waveform Sh not found in an adjacent frequency band is included in the frequency band of 0.2 to 0.3 Hz, the predetermined value may be set, for example, by experimentation, to the extent that the inclusion of the waveform Sh can be specified. The characteristic waveform Sh has, for example, an upwardly convex shape with a somewhat broad waveform (for example, a waveform having a total half width of 0.03 Hz or more). FIG. 3 illustrates an example of the first range R1 and the second range R2 in the frequency spectra FW1 and FW2 corresponding to stage 3.

On the other hand, in the frequency spectrum obtained from the subject in the stages of sleep of wakefulness, REM sleep, and stage 1, no significant intensity change is recognized in the frequency band of 0.2 to 0.3 Hz, and the characteristic waveform Sh as described above is also not observed.

After intensive research, the inventors have found that the subject is likely to be in stage 2 or 3 of sleep in a frequency spectrum in which a significant intensity change (characteristic waveform Sh) is observed in the frequency band of 0.2 to 0.3 Hz. That is, the inventors have found that in the frequency spectrum including the characteristic waveform Sh, the subject is likely to be in stage 2 or 3 of sleep. The inventors have also found that a significant intensity change is observed in the frequency band of 0.2 to 0.3 Hz especially in the frequency spectrum of the blood flow waveform data detected by the above-described blood flow meter (for example, the laser Doppler blood flow meter). Based on these findings, the inventors have developed a sleep estimation device that can improve the accuracy of determining the stage of sleep of a subject.

Comparison with Electrocardiographic Waveform Data

There are differences to be described below between electrocardiographic waveform data (electrocardiogram) detected by the electrocardiograph and blood flow waveform data detected by the blood flow meter.

Figure 4:
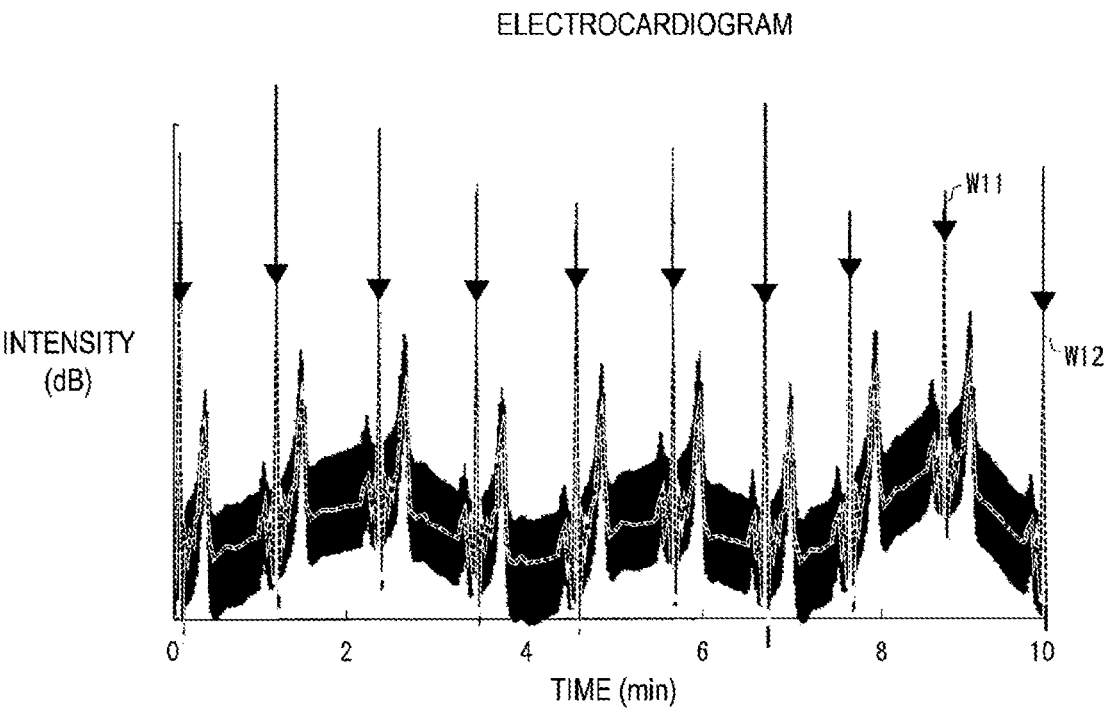
FIG. 4 is a graph showing an example of electrocardiographic waveform data detected by an electrocardiograph.

FIG. 4 is a graph showing an example of the electrocardiographic waveform data detected by the electrocardiograph. In FIG. 4, the vertical axis indicates the intensity of a heartbeat [units: dB] and the horizontal axis indicates measurement time [units: min]. FIG. 4 illustrates raw waveform data W11 and W12 of the heartbeat as the electrocardiographic waveform data.

Figure 5:
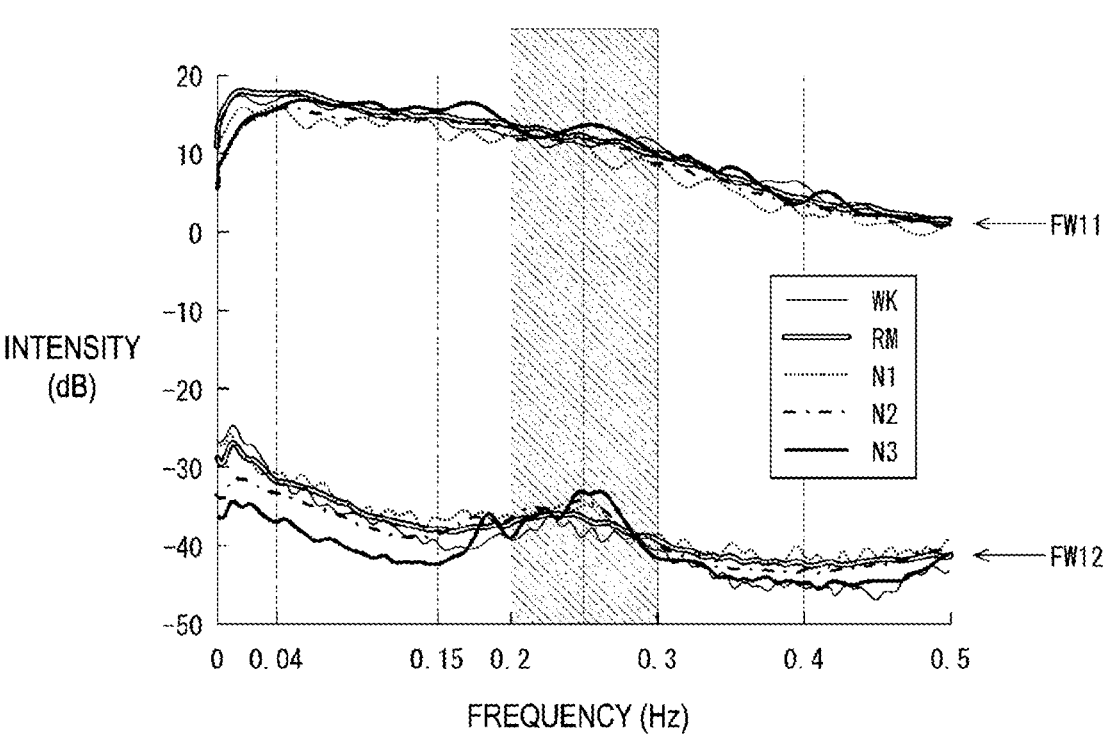
FIG. 5 is a graph showing an example of a frequency spectrum generated by performing Fourier transform processing on the electrocardiographic waveform data.

FIG. 5 is a graph showing an example of a frequency spectrum generated by performing Fourier transform processing on the electrocardiographic waveform data. The vertical axis indicates the intensity of a frequency spectrum [units: dB], and the horizontal axis indicates frequency [units: Hz].

FIG. 5 illustrates frequency spectra FW11 and FW12 corresponding to respective stages of sleep. The frequency spectrum FW11 is a frequency spectrum generated as a result of performing Fourier transform processing on the raw waveform data W11. The frequency spectrum FW12 is frequency spectrum generated as a result of performing Fourier transform processing on the heartbeat interval (RRI). The stages of sleep corresponding to the frequency spectra FW11 and FW12 are specified on the basis of the brain wave data acquired from the electroencephalograph attached to the subject.

As illustrated in FIG. 5, in the frequency spectra FW11 and FW12 obtained by converting the electrocardiographic waveform data detected from the subject who is in stages 2 and 3 of sleep, no significant intensity change (characteristic waveform Sh) is observed in the frequency band of 0.2 to 0.3 Hz. The frequency spectrum FW12 corresponding to stages 2 and 3 of sleep has an upwardly convex shape in the frequency band of 0.2 to 0.3 Hz. However, the frequency spectrum FW12 corresponding to stage 1 of sleep has a similar shape to the frequency spectrum FW12 corresponding to stages 2 and 3. Therefore, the fact that the frequency spectrum FW12 corresponding to stages 2 and 3 has a significant intensity change in the frequency band of 0.2 to 0.3 Hz is not observed.

After intensive research, the inventors have found that the significant intensity change recognized in the frequency band of 0.2 to 0.3 Hz is a phenomenon peculiar to the frequency spectrum of the blood flow waveform data. As a result, the inventors have found that when the stage of sleep of the subject is determined using a frequency spectrum converted from the blood flow waveform data instead of the electrocardiographic waveform data, the subject who is in, particularly, stage 2 or 3 of sleep can be accurately determined with a high probability.

Frequency Band

A frequency band in which the above significant intensity change is recognized may slightly spread depending on the blood flow meter used and individual differences in a subject. In view of this point, the significant intensity change not recognized in the electrocardiographic waveform data may be sufficiently observed in the frequency band of, for example, 0.15 to 0.4 Hz in the frequency spectra FW1 and FW2 corresponding to stage 2 or 3. The following description is given under the assumption that the frequency band in which the above significant intensity change is observed is 0.2 to 0.3 Hz.

Wavelet Transform Processing

The above principle has been described using the frequency spectrum obtained by performing the Fourier transform processing as the frequency analysis processing. However, the stage of sleep of the subject may be determined on the basis of a frequency spectrum obtained by performing wavelet transform processing as the frequency analysis processing. The wavelet transform processing is an example of time-frequency analysis processing. The time-frequency analysis processing is processing for generating a frequency spectrum of waveform data, including temporal changes. The wavelet transform processing is processing for generating a frequency spectrum of waveform data by using a mother wavelet that is an arbitrary reference waveform.

The mother wavelet used in the wavelet transform processing is defined as follows. In the following equation, "t" denotes a time variable, "a" denotes a scale parameter (parameter for expanding or contracting the mother wavelet in the time axis direction), and "b" denotes a translation parameter (parameter for translating the mother wavelet in the time axis direction).

$$\Psi_{a,b}(t) = \frac{1}{\sqrt{a}} \Psi\left(\frac{t-b}{a}\right) \qquad \text{Equation 1}$$

A function for performing the wavelet transform processing is also defined as follows. In the following equation, "f(t)" indicates waveform data and "*" indicates a conjugate complex number. By putting the mother wavelet having adjusted values of "a" and "b" into the following equation, a frequency spectrum of waveform data can be generated.

$$W_\psi(a, b) = \int_{-\infty}^{\infty} \Psi_{a,b}^*(t) f(t) dt \qquad \text{Equation 2}$$

By using the wavelet transform processing, an intensity (hereinafter, referred to as a target intensity) in the frequency band of 0.2 to 0.3 Hz can be relatively emphasized compared with other frequency bands. As described in the above principle, the subject is likely to be in stage 2 or 3 of sleep when a frequency spectrum having the characteristic waveform Sh in the frequency band of 0.2 to 0.3 Hz is obtained. Accordingly, by emphasizing the target intensity using the wavelet transform processing, the probability of more accurately determining whether the subject is in stage 2 or 3 of sleep can be increased.

In the wavelet transform processing, a mother wavelet set to emphasize the target intensity as described above may be used. A mother wavelet with an increased target intensity can be set by adjusting the values of "a" and "b". Morlet may also be used as the mother wavelet. In this case, the scale parameter "a" represents a local angular frequency having a relationship of "$\omega=2\pi/a$". Since the angular frequency "$\omega$" can be expressed as "$\omega=2\pi f$", the wavelet transform processing may be performed by setting a portion of the "f (frequency)" to 0.2 to 0.3 Hz. The target intensity may be an intensity in the entire frequency band of 0.2 to 0.3 Hz, or an intensity in a range (for example, the first range R1) which is a part of the frequency band.

As a result of the wavelet transform processing on the blood flow waveform data, intensity change data indicating temporal changes in intensity in each frequency band within a predetermined time can be generated. The predetermined time may be set, for example, by experimentation, to a time for which the stage of sleep of the subject can be accurately determined. In the present embodiment, the predetermined time may be set to 2.5 minutes, for example.

Unlike the Fourier transform processing, the wavelet transform processing can generate a frequency spectrum including temporal changes in intensity, leading to an increase in the number of data compared with the Fourier transform processing. Generally, in the generation of a learned model to be described below, a learned model can be generated to output more accurate output data as the number of data is increased (the number of characteristics to be learned is increased). Accordingly, using intensity change data is effective when the learned model is generated.

Figure 6:
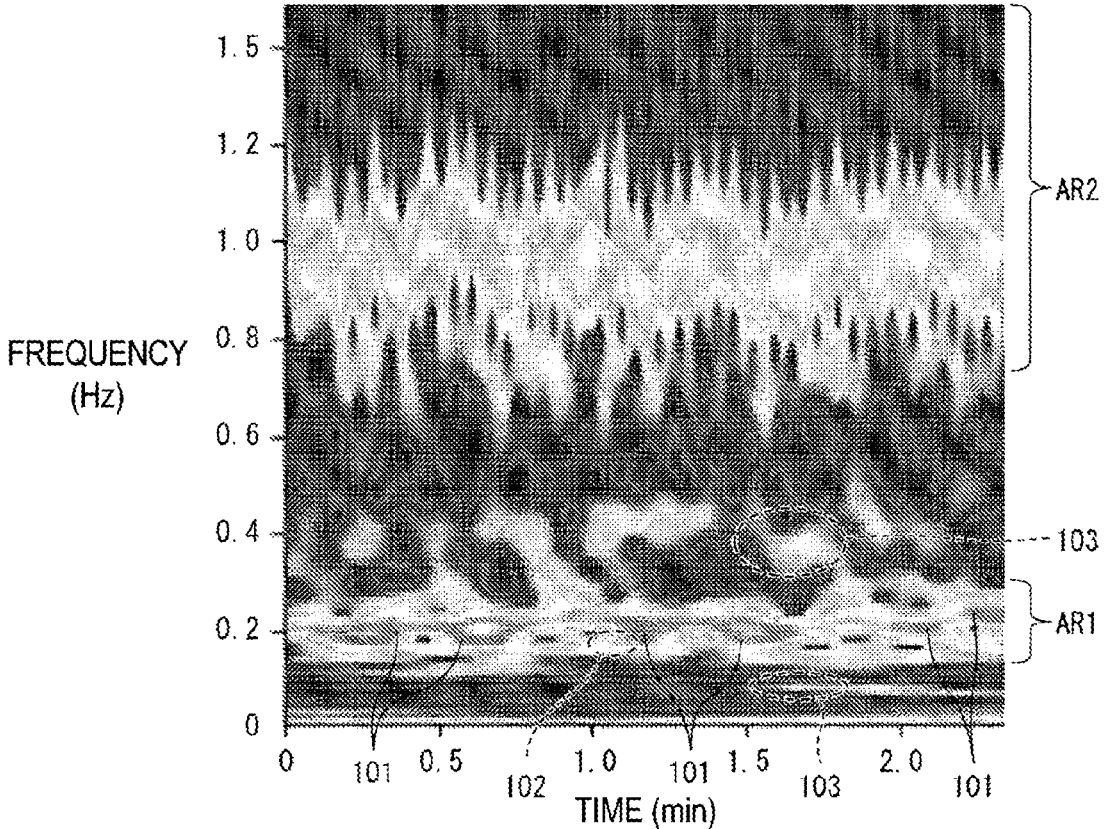
FIG. 6 is an image showing an example of a result of performing wavelet transform processing on the blood flow waveform data.

FIG. 6 is an image showing an example of a result of performing wavelet transform processing on blood flow waveform data. FIG. 6 illustrates an image generated by performing the wavelet transform processing on the blood flow waveform data (raw waveform data W1) serving as a basis of the frequency spectrum FW1 of the stage 3 shown in FIG. 3. The image is an example of intensity change data in which the target intensity is emphasized. Hereinafter, an image indicating the intensity change data is referred to as a wavelet image.

In FIG. 6, the vertical axis indicates frequency [units: Hz] and the horizontal axis indicates time [units: min]. Shading in the wavelet image in FIG. 6 indicates intensity [units: dB]. That is, the wavelet image is data indicating an intensity distribution of a frequency spectrum in a plane defined by frequency and time.

In the wavelet image of the present embodiment, a frequency band (intensity) may be expressed by color gradation. In the wavelet image, for example, a low frequency band can be expressed by cool colors and a high frequency band can be expressed by warm colors. Specifically, the frequency band may be expressed by dark blue, blue, light blue, yellowish green, pale yellowish green, yellow, orange, and red in descending order. When the intensity distribution can be visibly recognized in the wavelet image, the frequency band may be expressed in other colors, or may be expressed by grayscale. FIG. 6 illustrates an example of a grayscale image of the wavelet image expressed in the above colors.

In the wavelet image in FIG. 6, a first region AR1 distributed along the time axis at and around 0.2 Hz exhibits a higher intensity than a frequency band adjacent to the first region AR1. Specifically, in a frequency band of about 0.2 Hz±about 0.05 Hz in the first region AR1, an intensity band indicated by red is distributed along the time axis, and an intensity region indicated by orange, yellow, pale yellowish green, and yellowish green is distributed around the intensity band. In FIG. 6, reference sign 101 denotes a part of the intensity band indicated by red. Reference sign 102 denotes a part of the intensity region indicated by orange, yellow, pale yellowish green, and yellowish green. On the other hand, in adjacent frequency bands, an intensity region indicated by light blue, blue, and dark blue is mainly distributed, but an intensity region indicated by red, orange, and yellow is not distributed. In FIG. 6, reference sign 103 denotes a part of the intensity region indicated by light blue, blue, and dark blue.

As illustrated in FIG. 6, in the wavelet image, a saw-shaped intensity band is formed along the time axis in a frequency band higher than the frequency band of 0.2 to 0.3 Hz. In the wavelet image in FIG. 6, the saw-shaped intensity band is formed in the second region AR2 (frequency band of about 0.7 Hz or higher). The second region AR2 has a lower intensity than the first region AR1 in a frequency band of about 0.9 to 1.0 Hz, and is gradually reduced in intensity toward a frequency band of less than 0.9 Hz and a frequency band of 1.0 Hz or higher.

The saw-shaped intensity band indicates an intensity distribution corresponding to the heartbeat. The intensity distribution has a band shape along the time axis in a sleep state, and as the sleep becomes shallower, the band shape becomes more deformed. The intensity distribution corresponding to the heartbeat is an intensity distribution that is not obtained by the Fourier transform processing. By using a wavelet image to generate a learned model to be described below, a learned model that considers a heartbeat can be generated.

FIG. 6 illustrates an example of the wavelet image in which the target intensity is emphasized, but it is noted that even in a wavelet image in which the target intensity is not emphasized, the intensity of the first region AR1 is higher than the intensity in an adjacent frequency band.

Generation of Learned Model

In determining the stage of sleep of a subject, a learned model (approximator) for determining the stage of sleep of the subject can be used. The learned model is a mathematical model (neural network including an input layer, a hidden layer, and an output layer) that imitates neurons of the human cranial nervous system and is trained to be able to determine the stage of sleep of a user. Any mathematical model is used as long as it can generate a learned model capable of determining the stage of sleep of the subject. The mathematical model may be, for example, a convolutional neural network (CNN), a recurrent neural network (RNN), or a long short term memory (LSTM).

The learning refers to adjusting the strength of connection between units, a bias of the connection, and the like so that a correct operation result is output from the output layer. In the present embodiment, when the learning is performed, learning data is input to the input layer. In the hidden layer, an operation based on operation data is performed on the learning data, and an operation result in the hidden layer is output from the output layer as output data. Teacher data and the output data are compared, and the operation data is adjusted so that an error is reduced. A learned model, in which the operation data is adjusted by repeatedly performing the process for each of a plurality of learning data, is generated. That is, in the present embodiment, the learned model may be generated by so-called supervised learning using the learning data and the teacher data. A sleep estimation device 51 to be described below can determine the stage of sleep of the subject by using the learned model generated in this manner.

The learning data is data serving as an example for generating the learned model. The learning data may be a frequency spectrum generated from blood flow waveform data. In the present embodiment, a wavelet image is used. The wavelet image may be one in which a target intensity is emphasized or one in which in a target intensity is not emphasized. The learning data may have different behaviors during wakefulness and during sleep, or may have behaviors that change according to the depth of sleep. The learning data may be various types of data (for example, frequency spectra of blood flow waveform data indicating mutually different waveforms).

The teacher data is data in which a correct answer label is associated with the learning data. For example, data, in which the stage of sleep of a person who has acquired blood flow waveform data is associated as a correct answer label with a frequency spectrum serving as learning data, may be used as teacher data. As described above, the stage of sleep of the subject may be specified on the basis of the brain wave data detected by the electroencephalograph. As the correct answer label, a code indicating each stage of sleep may be used. Alternatively, as the correct answer label, a code indicating a correct answer may be used for a specific stage of sleep (for example, stage 2 or 3), and a code indicating an incorrect answer may be used for other stages of sleep. In the present embodiment, as an example of the teacher data, data associated as a correct answer label with a wavelet image (wavelet image specified as stage 2 or 3 by brain wave data) known to correspond to stage 2 or 3 may be used.

The operation data is data related to an operation for generating a learned model, including data such as an operation formula, variables (for example, bias and weight) of the operation formula, and an activation function. The bias and the weight define the strength of connection between units. By adjusting the bias and the weight, the accuracy of the learned model can be increased. As a method of adjusting the operation data, for example, a back propagation method and a gradient descent method may be employed.

First Embodiment

An example of a sleep estimation system 1 capable of determining the stage of sleep of a subject, which is constructed on the basis of the above principle, is described below. The sleep estimation system 1 of the present embodiment may be a system capable of determining the stage of sleep of a subject by using the above learned model.

Sleep Stage Estimation System

Figure 1:
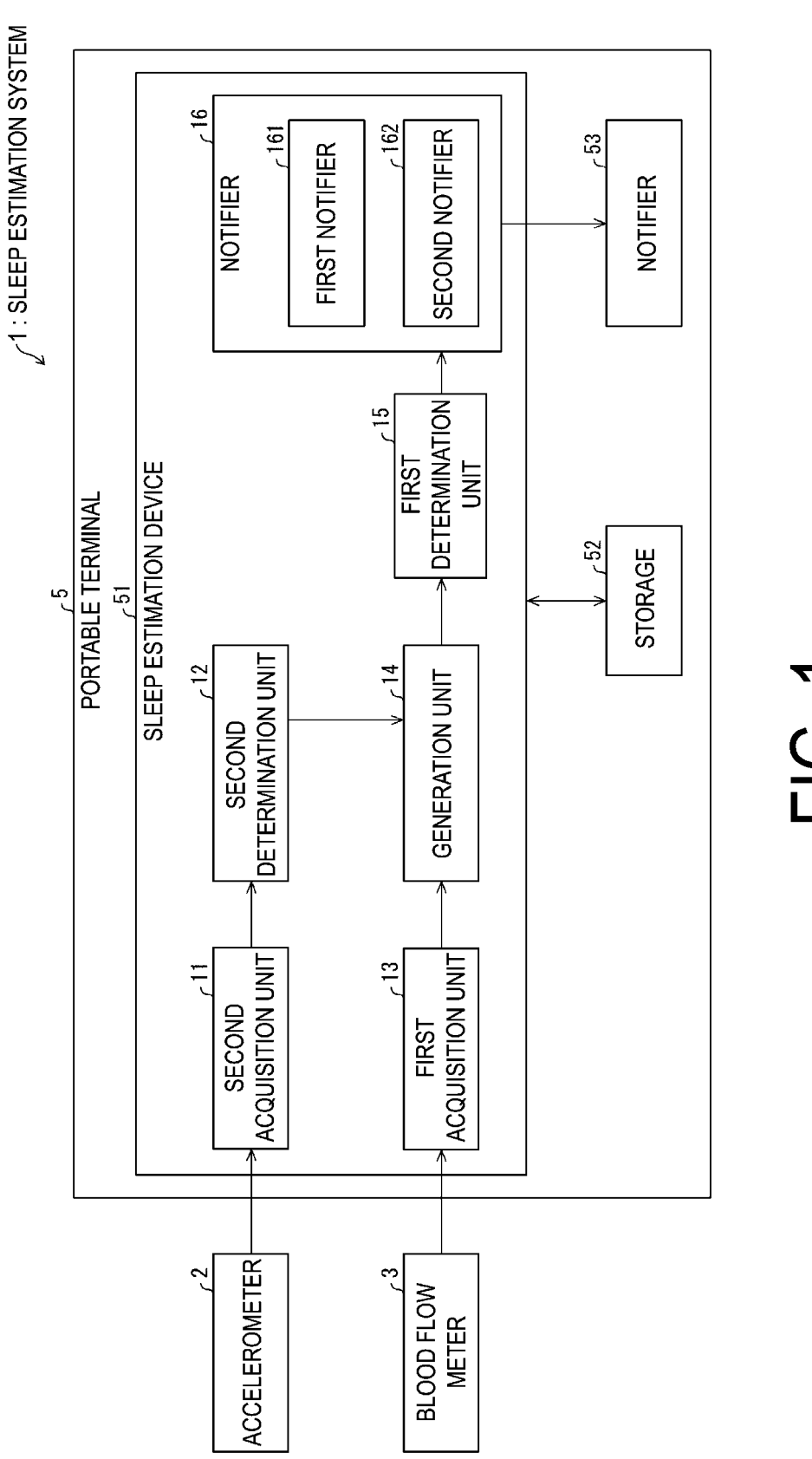
FIG. 1 is a block diagram illustrating a schematic configuration example of a sleep estimation system of a first embodiment.

FIG. 1 is a block diagram illustrating a schematic configuration example of the sleep estimation system 1 of the first embodiment. As illustrated in FIG. 1, the sleep estimation system 1 includes an accelerometer 2, a blood flow meter 3, and a portable terminal 5. In the portable terminal 5, as a part of the function of a control unit for comprehensively controlling each member of the portable terminal 5, for example, the sleep estimation device 51 is constructed to determine the stage of sleep of a subject by executing an application capable of determining the stage of sleep of the subject.

Accelerometer

The accelerometer 2 is a sensor capable of detecting an acceleration caused by the movement of the subject. The accelerometer 2 may transmit the detected acceleration to the sleep estimation device 51 as acceleration data by wireless or wired communication. The accelerometer 2 is attached to a part of a body of the subject, such as a head or a finger, for example. A known sensor such as a frequency change type sensor, a piezoelectric sensor, a piezoresistive sensor, or a capacitive sensor may be used as the accelerometer 2.

Blood Flow Meter

The blood flow meter 3 may be a blood flow meter described in the above principle. The blood flow meter 3 may be, for example, a laser Doppler blood flow meter. In the present embodiment, the blood flow meter 3 may transmit the raw waveform data W1 as blood flow waveform data to the sleep estimation device 51. The blood flow meter 3 may transmit, instead of the raw waveform data W1, the processed waveform data W2 to the sleep estimation device 51. The blood flow meter 3 need not generate the processed waveform data W2, and the sleep estimation device 51 may generate the processed waveform data W2. The blood flow meter 3 is attached to a part of the body of the subject, such as the ear, finger, wrist, arm, forehead, nose, or neck.

Portable Terminal

The portable terminal 5 may be a terminal capable of performing data communication with at least the accelerometer 2 and the blood flow meter 3. The portable terminal 5 may be, for example, a smartphone or a tablet. The portable terminal 5 is equipped with the sleep estimation device 51, and includes a storage 52 and a notifier 53.

The storage 52 can store programs and data to be used by the control unit (particularly, the sleep estimation device 51). The storage 52 can store, for example, the learned model generated as described above and a threshold value for determining whether the subject is stationary.

The notifier 53 can notify the surroundings of the portable terminal 5 (for example, the subject) of various information. In the present embodiment, the notifier 53 can notify various information according to notification instructions from the sleep estimation device 51. The notifier 53 may be at least any of a sound output device for outputting sound, a vibration device for vibrating the portable terminal 5, and a display device for displaying an image.

Sleep Estimation Device

The sleep estimation device 51 can determine the stage of sleep of the subject who is wearing the accelerometer 2 and the blood flow meter 3. The sleep estimation device 51 may include a second acquisition unit 11, a second determination unit 12, a first acquisition unit 13 (acquisition unit), a generation unit 14, a first determination unit 15 (determination unit), and a notifier 16.

The second acquisition unit 11 can acquire acceleration data from the accelerometer 2. The second determination unit 12 can determine whether the subject is stationary, on the basis of the acceleration data acquired by the second acquisition unit 11. For example, when the acceleration indicated by the acceleration data is less than the threshold value stored in the storage 52, the second determination unit 12 may determine that the subject is stationary. The second determination unit 12 may transmit determination result data to the generation unit 14.

The first acquisition unit 13 can acquire blood flow waveform data (raw waveform data W1) from the blood flow meter 3. The generation unit 14 can generate a frequency spectrum of the blood flow waveform data by performing frequency analysis processing on the blood flow waveform data acquired by the first acquisition unit 13. The first determination unit 15 can determine the stage of sleep of the subject on the basis of the frequency spectrum generated by the generation unit 14. In other words, the first determination unit 15 can determine the transition of the depth of sleep of the subject on the basis of the frequency spectrum.

In the present embodiment, the generation unit 14 can generate a wavelet image by performing, as the frequency analysis processing, wavelet transform processing in which a target intensity is relatively emphasized compared with other frequency bands. The wavelet image is processed data indicating the result of time-frequency analysis processing on the blood flow waveform data. The first determination unit 15 can determine the stage of sleep of the subject on the basis of the wavelet image generated by the generation unit 14.

In the present embodiment, when the first determination unit 15 determines that the characteristic waveform Sh is included in the frequency band of 0.2 to 0.3 Hz in the frequency spectrum, the first determination unit 15 can determine that the stage of sleep of the subject is stage 2 or 3. In this case, the first determination unit 15 may determine that the stage of sleep of the subject has transitioned from stage 1 to stage 2 or 3. On the other hand, when the first determination unit 15 determines that the characteristic waveform Sh is not included in the frequency band of 0.2 to 0.3 Hz, the first determination unit 15 can determine that the stage of sleep of the subject is a stage of sleep other than stage 2 or 3. When the first determination unit 15 determines that the characteristic waveform Sh is not included in the frequency band of 0.2 to 0.3 Hz after determining that the subject is in stage 2 or 3 of sleep, the first determination unit 15 may determine that the stage of sleep of the subject has transitioned from stage 2 or 3 to stage 1. The determination regarding whether the characteristic waveform Sh is included can be performed by, for example, determining whether the first intensity is greater than the second intensity by a predetermined value or more.

In the present embodiment, the first determination unit 15 may determine the stage of sleep of the subject by using a learned model. In this case, the first determination unit 15 can output the determination result for the stage of sleep of the subject from the output layer of the learned model by adding, as input data, the wavelet image generated by the generation unit 14 to the input layer of the learned model.

As described above, the learned model is generated using, as an example of the teacher data, the data associated as a correct answer label with the wavelet image known to correspond to stage 2 or 3. Therefore, by adding the wavelet image generated by the generation unit 14 to the learned model, the first determination unit 15 can determine that the stage of sleep of the subject is stage 2 or 3 or that the stage of sleep of the subject has transitioned from stage 1 to stage 2 or 3. Particularly, when a frequency spectrum including the characteristic waveform Sh in the frequency band of 0.2 to 0.3 Hz is added to the learned model, the first determination unit 15 may accurately determine that the stage of sleep of the subject is stage 2 or 3.

When the stage of sleep is estimated using the blood flow waveform data, the sleep estimation device may not be able to determine whether the subject is falling asleep only by the blood flow waveform data. For example, in the case of a subject whose blood flow is stable even when awake, a significant difference may not be observed between blood flow waveform data during wakefulness and blood flow waveform data during sleep, and in this case, the sleep estimation device may not be able to determine whether the subject is falling asleep. In the present embodiment, when the second determination unit 12 determines that the subject is stationary, the generation unit 14 can perform the determination process by the first determination unit 15 in a state in which the subject is likely to have fallen asleep by performing frequency analysis processing on the blood flow waveform data.

The notifier 16 can perform notification processing based on the determination result of the first determination unit 15. The notifier 16 may transmit a notification instruction according to the notification processing to the notifier 53. Thus, the notifier 53 can notify the surroundings of the portable terminal 5 of information according to the notification processing. The notifier 16 may include a first notifier 161 and a second notifier 162.

The first notifier 161 can perform first notification processing as the above notification processing after the first determination unit 15 detects a transition from stage 1 to stage 2 or 3 and a predetermined time elapses. The first notification processing is a notification process associated with the detection of the transition, and for example, may be an alarm process for promoting the subject to wake up, or a process for notifying the detection of the transition. The predetermined time may be appropriately set by, for example, an experiment according to the purpose of the notification. In the present embodiment, the predetermined time may be set to a time that is estimated to make the subject more likely to wake up when measured from the point of transition from stage 1 to stage 2 or 3, for example. By the first notification processing, for example, the subject can wake up at a good awakening timing after falling asleep. The first notifier 161 may perform the first notification processing when the first determination unit 15 detects the transition from stage 1 to stage 2 or 3.

The second notifier 162 can perform second notification processing as the above notification processing after the first determination unit 15 detects a transition from stage 2 or 3 to stage 1 and a predetermined time elapses. The second notification processing is a notification process associated with the detection of the transition, and for example, may be an alarm process for prompting the subject to wake up, or a process for notifying the detection of the transition. The predetermined time may be appropriately set by, for example, an experiment according to the purpose of the notification. In the present embodiment, the predetermined time may be set to a time that is estimated to make the subject more likely to wake up when measured from the point of transition from stage 2 or 3 to stage 1, for example. By the second notification processing, for example, the subject can wake up at a good awakening timing after having fallen asleep. The second notifier 162 may perform the second notification processing when the first determination unit 15 detects the transition from stage 2 or 3 to stage 1.

Processing Flow

Figure 7:
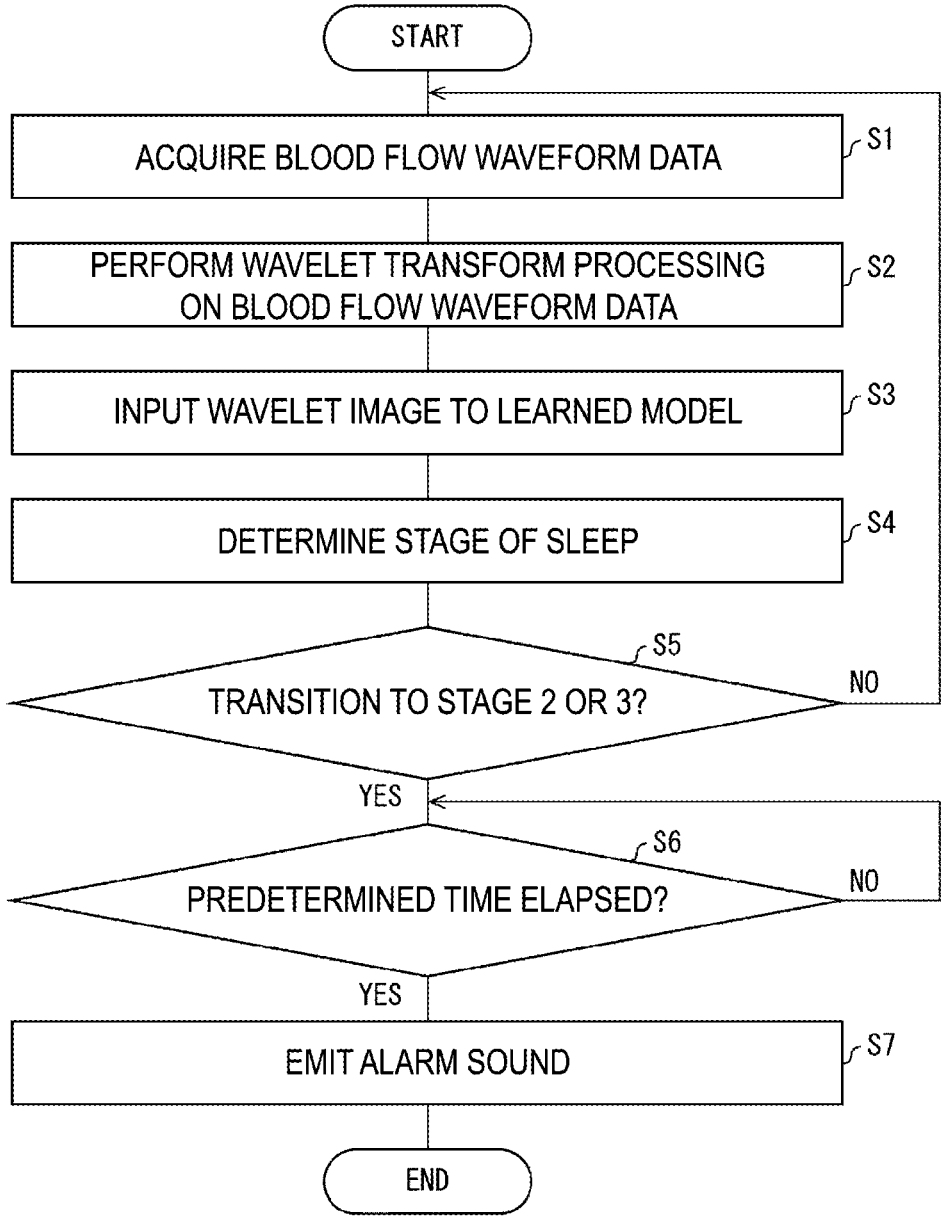
FIG. 7 is a flowchart illustrating an example of the flow of processing performed by a sleep estimation device of the first embodiment.

FIG. 7 is a flowchart illustrating an example of the flow (sleep estimation method) of processing performed by the sleep estimation device 51. When the sleep estimation device 51 determines the stage of sleep of the subject, after the blood flow meter 3 is attached to the subject, the blood flow meter 3 may start detecting blood flow waveform data.

As illustrated in FIG. 7, in the sleep estimation device 51, the first acquisition unit 13 can acquire blood flow waveform data from the blood flow meter 3 (S1: first acquisition step, acquisition step). The generation unit 14 can generate the frequency spectrum of the blood flow waveform data by performing frequency analysis processing on the blood flow waveform data. In the present embodiment, the generation unit 14 can generate the wavelet image, in which the target intensity is emphasized, by performing the wavelet transform processing on the blood flow waveform data (S2: generation step). The first determination unit 15 can determine the stage of sleep of the subject on the basis of the frequency spectrum. In the present embodiment, the first determination unit 15 can input the wavelet image in which the target intensity is emphasized into the learned model (S3), thereby determining the stage of sleep of the subject (S4: first determination step, determination step).

On the basis of the determination result for the stage of sleep, the first determination unit 15 can determine whether the stage of sleep has transitioned from stage 1 to stage 2 or 3 (S5). When the first determination unit 15 determines that the stage of sleep has transitioned from stage 1 to stage 2 or 3 (YES at S5), the first notifier 161 can determine whether the predetermined time has elapsed from the determination (S6). When the first notifier 161 determines that the predetermined time has elapsed (YES at S6), the first notifier 161 can perform, as the first notification processing, an alarm process for causing the notifier 53 to emit an alarm sound, for example (S7). Upon receiving a notification instruction from the first notifier 161, the notifier 53 can emit an alarm sound.

When NO at S5, the procedure may return to the process of S1. When NO at S6, the process of S6 may be repeated. When the first determination unit 15 determines that the stage of sleep has transitioned from stage 2 or 3 to stage 1 at S5, the second notifier 162 may perform the second notification processing, for example, after the predetermined time elapses.

Problem in Related Art and Effect of Sleep Estimation Device According to Present Disclosure Patent Document 1 discloses a method for detecting non-REM sleep including the following steps 1 to 4.

Step 1: step of generating time-series data of the beat interval of the heart of a subject.

Step 2: step of setting a prescribed time length window moving along the time axis of the time-series data and performing, regarding each of a plurality of determination points on the time axis, spectrum analysis on the time-series data in windows including the determination points.

Step 3: step of calculating a degree of concentration of power of heartbeat fluctuation high-frequency components from the spectrum of each of the windows.

Step of determining whether sleep is non-REM sleep on the basis of the calculated degree of concentration.

In the above method, for example, a pulse wave meter or an electrocardiograph is used as a device for detecting the time-series data of step 1.

However, handling an electroencephalograph and acquisition of brain waves require highly specialized knowledge. In addition, attachment of an electroencephalograph is complicated. Acquisition of brain waves is difficult, and it is difficult for the subject to easily ascertain his/her stage of sleep.

As described above, the inventors have found that when a significant intensity change is recognized in the frequency spectrum of 0.2 to 0.3 Hz in the frequency band of the blood flow waveform data, the subject is likely to be in stage 2 or 3 of sleep.

The sleep estimation device 51 of the present disclosure can determine the stage of sleep of the subject by using the blood flow waveform data. In comparison with the electro-encephalograph, handling the blood flow meter and acquiring the blood flow waveform data do not require highly specialized knowledge. In addition, the attachment of the blood flow meter is easier than the attachment of the electroencephalograph. That is, the sleep estimation device 51 can relatively easily acquire the blood flow waveform data of the subject, thereby relatively easily determining the stage of sleep of the subject. According to the sleep estimation device 51, the subject can easily ascertain his/her stage of sleep.

When a frequency spectrum having the above significant intensity change not found in the electrocardiographic waveform data is obtained, the sleep estimation device 51 of the present disclosure can determine that the stage of sleep of the subject is stage 2 or 3. Therefore, the likelihood that the sleep estimation device 51 can accurately estimate the stage of sleep of the subject to be stage 2 or 3 can be increased.

Second Embodiment

Figure 8:
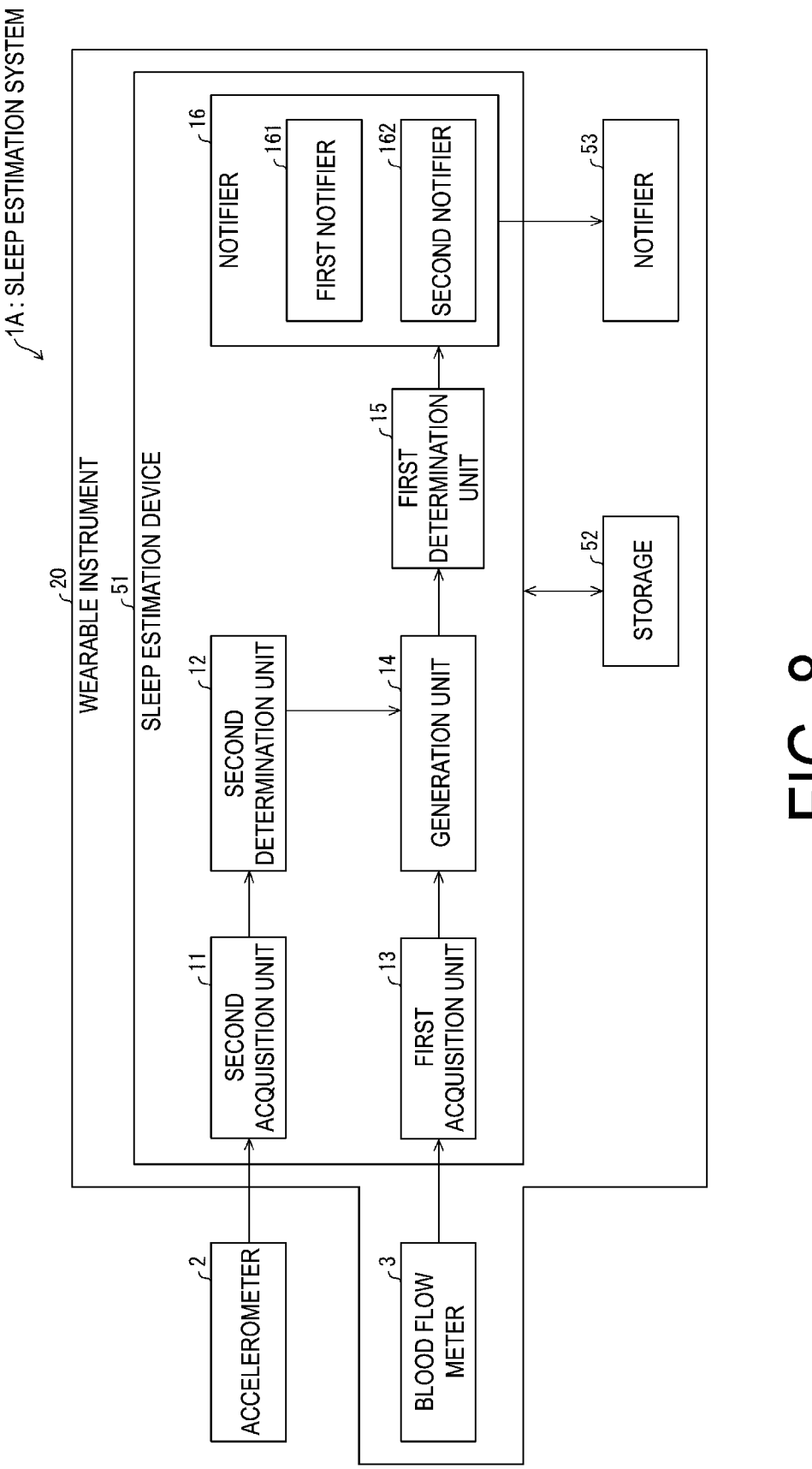
FIG. 8 is a block diagram illustrating a schematic configuration example of a sleep estimation system of a second embodiment.

Another embodiment of the present disclosure will be described below. Note that, for convenience of description, a member having the same function as that of a member described in the embodiments described above is denoted by the same reference sign, and description thereof will not be repeated. FIG. 8 is a block diagram illustrating a schematic configuration example of a sleep estimation system 1A of a second embodiment.

In the sleep estimation system 1 of the first embodiment, the portable terminal 5 can acquire the blood flow waveform data from the blood flow meter 3 attached to the subject, for example, by wireless communication. Then, the sleep estimation device 51 built in the portable terminal 5 can determine the stage of sleep of the subject on the basis of the blood flow waveform data.

On the other hand, as illustrated in FIG. 8, in the sleep estimation system 1A of the second embodiment, a wearable instrument 20 may be provided with the blood flow meter 3. In addition, in the wearable instrument 20, the sleep estimation device 51 may be constructed as a part of the function of a control unit that comprehensively controls each member of the wearable instrument 20. That is, in the sleep estimation system 1A, the sleep estimation device 51 may be attached to the wearable instrument 20 together with the blood flow meter 3. Therefore, one instrument can perform the process of acquiring the blood flow waveform data, and the process of determining the stage of sleep based on the blood flow waveform data. Furthermore, various instruments, components, and the like required when performing wireless or wired communication between two instruments are not required. The wearable instrument 20 may be attached to the same position as the position where the blood flow meter 3 is attached to the subject.

Variation

In the present disclosure, the invention has been described above based on the various drawings and examples. However, the invention according to the present disclosure is not limited to each embodiment described above. That is, the embodiments of the invention according to the present disclosure can be modified in various ways within the scope illustrated in the present disclosure, and embodiments obtained by appropriately combining the technical means disclosed in different embodiments are also included in the technical scope of the invention according to the present disclosure. In other words, note that a person skilled in the art can easily make various variations or modifications based on the present disclosure. Note that these variations or modifications are included within the scope of the present disclosure.

Variation of Frequency Analysis Processing

For example, the generation unit 14 may be able to generate a wavelet transform image by performing the wavelet transform processing on the blood flow waveform data, and does not necessarily have to perform the wavelet transform processing so that the target intensity is emphasized.

The generation unit 14 may also perform time-frequency analysis processing, other than the wavelet transform processing, on the blood flow waveform data. The generation unit 14 may perform, for example, short-time Fourier transform processing on the blood flow waveform data. The short-time Fourier transform processing involves performing Fourier transform processing on each of a plurality of waveform data cut along a time axis by using a window function. In this case, the generation unit 14 may generate, as processed data, an image (intensity change data) similar to the wavelet image by performing short-time Fourier transform processing in which the target intensity is relatively emphasized compared with other frequency bands.

The generation unit 14 may also perform processing, other than the time-frequency analysis processing, as the frequency analysis processing. The generation unit 14 may perform Fourier transform processing, for example. When the generation unit 14 performs Fourier transform processing, for example, the frequency spectrum FW1 or FW2 illustrated in FIG. 3 can be generated. The generation unit 14 may also generate a frequency spectrum (waveform) as illustrated in FIG. 3 by performing short-time Fourier transform processing.

In this way, the generation unit 14 can generate various frequency spectra. Accordingly, the first determination unit 15 can determine the stage of sleep of the subject by inputting various frequency spectra into a learned model. However, the learned model is generated using the same kind of frequency spectrum as the frequency spectrum, which is generated by the generation unit 14, as learning data and teacher data.

Variation of Determination Processing of First Determination Unit

The learned model need not be stored in the storage 52 of the portable terminal 5 or the wearable instrument 20. That is, the sleep estimation system 1 or 1A need not determine the stage of sleep of the subject by using the learned model.

For example, when the first determination unit 15 determines that the first intensity is greater than the second intensity by the predetermined value or more in the frequency spectrum generated by the generation unit 14, the stage of sleep of the subject may be determined to be stage 2 or 3. The storage 52 may store the predetermined value instead of the learned model.

Once the first determination unit 15 determines the stage of sleep of the subject by using the frequency spectrum FW1, the first determination unit 15 may determine that the stage of sleep of the subject is stage 2 or 3 when the characteristic waveform Sh can be extracted in the frequency band of 0.2 to 0.3 Hz. In this case, the storage 52 may store a reference waveform, by which the characteristic waveform Sh can be extracted in the frequency spectrum FW1, instead of the learned model. When the first determination unit 15 determines that a waveform matching the reference waveform exists in the frequency band of 0.2 to 0.3 Hz in the frequency spectrum FW1, the first determination unit 15 may determine that the characteristic waveform Sh can be extracted in the frequency band. When the degree of matching between a waveform included in the frequency band of 0.2 to 0.3 Hz and the reference waveform is equal to or greater than a threshold value set by, for example, experimentation, the first determination unit 15 may determine that the waveform matching the reference waveform exists in the frequency band of 0.2 to 0.3 Hz. On the basis of another index (for example, the degree of change in the slope of a waveform), the first determination unit 15 may also determine whether the characteristic waveform Sh is included in the frequency band of 0.2 to 0.3 Hz. The same determination as in the frequency spectrum FW1 may be performed for the frequency spectrum FW2.

Variation of Sleep Estimation System 1 or 1A

The accelerometer 2 may detect an acceleration caused by the movement of the subject, and the sleep estimation device 51 need not determine the somnolent state of the subject on the basis of the acceleration. In this case, the sleep estimation system 1 or 1A need not include the accelerometer 2, and the sleep estimation device 51 need not include the second acquisition unit 11 and the second determination unit 12.

Example of Software Implementation

A control block of the sleep estimation device 51 may be implemented by a logic circuit (hardware) formed in an integrated circuit (IC chip) or the like, or may be implemented by software.

In the latter case, the sleep estimation device 51 includes a computer that executes instructions of a program that is software for implementing each function. The computer includes, for example, at least one processor (control device) and at least one computer-readable recording medium storing the above program. Then, in the computer, the processor reads the above program from the recording medium and executes the read program to achieve the object of the present disclosure. As the processor, a central processing unit (CPU) can be used, for example. As the recording medium, a "non-transitory tangible medium" such as, for example, a read only memory (ROM), a tape, a disk, a card, a semiconductor memory, a programmable logic circuit, and the like can be used. Additionally, a random access memory (RAM) for loading the above program may be further provided. The above program may be supplied to the computer via any transmission medium (communication network, broadcast wave, and the like) capable of transmitting the program. Further, one aspect of the present disclosure may be implemented in the form of data signals embedded in a carrier wave in which the above program is embodied by electronic transmission.

REFERENCE SIGNS

1, 1A Sleep estimation system
3 Blood flow meter
11 Second acquisition unit
12 Second determination unit
13 First acquisition unit (acquisition unit)
14 Generation unit
15 First determination unit (determination unit)
20 Wearable instrument
51 Sleep estimation Device
161 First notifier
162 Second notifier

The invention claimed is:

1. A sleep estimation device comprising:

a processor that executes the following functions:

acquiring blood flow data indicating a blood flow of a subject;

generating a frequency spectrum of the blood flow data by performing frequency analysis processing on the blood flow data; and determining a stage of sleep of the subject based on the frequency spectrum, wherein when the stage of sleep in non-REM sleep is classified into stages 1 to 3 comprising a stage 1, a stage 2 and a stage 3, in an order from a lightest stage of sleep, the processor determines that the stage of sleep of the subject has transitioned from stage 1 to stage 2 or stage 3 in a case where a frequency band of 0.2 to 0.3 Hz is divided into a first range and a second range and the generated frequency spectrum has a first intensity that is a maximum intensity in the first range and a second intensity that is a maximum intensity in the second range and the first intensity is larger than the second intensity.

2. The sleep estimation device according to claim 1, wherein the processor is further configured to execute the function:

performing first notification processing subsequent to determining that the stage of sleep of the subject has transitioned from the stage 1 to the stage 2 or the stage 3, or subsequent to determining that the stage of sleep of the subject has transitioned from the stage 1 to the stage 2 or the stage 3 and a predetermined time has elapsed.

3. The sleep estimation device according to claim 1, wherein the processor is further configured to execute the functions:

generating, as the frequency spectrum, intensity change data indicating a temporal change in intensity in each frequency band within a predetermined time by performing time-frequency analysis processing as the frequency analysis processing, and adding the intensity change data to a learned model, the learned model learned using teacher data in which a correct answer label is associated with the intensity change data known to correspond to the stage 2 or the stage 3, thereby determining that the stage of sleep of the subject has transitioned from the stage 1 to the stage 2 or the stage 3.

4. The sleep estimation device according to claim 1, wherein the processor is further configured to execute the functions:

acquiring acceleration data indicating an acceleration caused by a movement of the subject; and determining whether the subject is stationary based on the acceleration data, wherein the frequency analysis processing is performed when the subject is stationary.

5. A sleep estimation device comprising:

a blood flow meter comprising a light emitting unit configured to irradiate a blood vessel of the subject with light, and a light receiving unit configured to receive scattered light generated by the irradiation;

a processor that executes the following functions:

acquiring blood flow data from the blood flow meter, the blood flow data indicating a blood flow of a subject based on the received scattered light;

generating a frequency spectrum indicating a result of time-frequency analysis processing on the blood flow data by performing wavelet transform processing or short-time Fourier transform processing, in which an intensity in a predetermined frequency band is relatively emphasized compared with other frequency bands, on the blood flow data; and determining a stage of sleep of the subject based on the frequency spectrum, wherein when the stage of sleep in non-REM sleep is classified into stages 1 to 3 comprising a stage 1, a stage 2 and a stage 3, in an order from a lightest stage of sleep, the processor determines that the stage of sleep of the subject has transitioned from stage 1 to stage 2 or stage 3 in a case where a frequency band of 0.2 to 0.3 Hz is divided into a first range and a second range and the generated frequency spectrum has a first intensity that is a maximum intensity in the first range and a second intensity that is a maximum intensity in the second range and the first intensity is larger than the second intensity.

6. The sleep estimation device according to claim 5, wherein the processor is further configured to execute the functions:

generating, as the frequency spectrum, intensity change data indicating a temporal change in intensity in each frequency band within a predetermined time, and adding the intensity change data to a learned model, the learned model learned using teacher data in which a correct answer label is associated with the intensity change data known to correspond to the stage 2 or the stage 3, thereby determining that the stage of sleep of the subject has transitioned from the stage 1 to the stage 2 or the stage 3.

7. A sleep estimation system comprising:

a portable terminal including the sleep estimation device according to claim 1; and a blood flow meter that detects the blood flow data by receiving scattered light generated by irradiating a blood vessel of the subject with light.

8. A wearable instrument comprising:

the sleep estimation device according to claim 1; and a blood flow meter that detects the blood flow data by receiving scattered light generated by irradiating a blood vessel of the subject with light.

9. A sleep estimation method comprising:

detecting blood flow data by irradiating a blood vessel of a subject with light and receiving scattered light generated by the irradiation, wherein the blood flow data indicates a blood flow of the subject;

generating a frequency spectrum of the blood flow data by performing frequency analysis processing on the blood flow data;

determining a stage of sleep of the subject based on the frequency spectrum, wherein when the stage of sleep in non-REM sleep is classified into stages 1 to 3 comprising a stage 1, a stage 2 and a stage 3, in an order from a lightest stage of sleep;

dividing a frequency band of 0.2 to 0.3 Hz into a first range and a second range;

determining a first intensity that is a maximum intensity in the first range and a second intensity that is a maximum intensity in the second range; and determining that the stage of sleep of the subject has transitioned from stage 1 to stage 2 or stage 3 based on the first intensity being larger than the second intensity.

10. A sleep estimation method comprising:

acquiring blood flow data indicating a blood flow of a subject;

generating a frequency spectrum indicating a result of time-frequency analysis processing on the blood flow data by performing wavelet transform processing or short-time Fourier transform processing, in which an intensity in a predetermined frequency band is relatively emphasized compared with other frequency bands, on the blood flow data;

determining a stage of sleep of the subject based on the frequency spectrum, wherein when the stage of sleep in non-REM sleep is classified into stages 1 to 3 comprising a stage 1, a stage 2 and a stage 3, in an order from a lightest stage of sleep;

dividing a frequency band of 0.2 to 0.3 Hz into a first range and a second range;

determining a first intensity that is a maximum intensity in the first range and a second intensity that is a maximum intensity in the second range; and determining that the stage of sleep of the subject has transitioned from stage 1 to stage 2 or stage 3 based on the first intensity being larger than the second intensity.

* * * * *